(12) United States Patent
Danek et al.

(10) Patent No.: US 7,594,925 B2
(45) Date of Patent: Sep. 29, 2009

(54) CONTROL SYSTEMS FOR DELIVERING ENERGY

(75) Inventors: Christopher J. Danek, San Carlos, CA (US); William J. Wizeman, Mountain View, CA (US); Tim R. Dalbec, Saratoga, CA (US); Glendon E. French, San Mateo, CA (US); Michael D. Laufer, Menlo Park, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 376 days.

(21) Appl. No.: 11/408,668

(22) Filed: Apr. 21, 2006

(65) Prior Publication Data

US 2006/0247683 A1 Nov. 2, 2006

Related U.S. Application Data

(60) Provisional application No. 60/673,876, filed on Apr. 21, 2005.

(51) Int. Cl.
*A61B 18/18* (2006.01)

(52) U.S. Cl. .............................. 607/96; 607/2; 607/113; 606/41

(58) Field of Classification Search ................ 600/381, 600/437, 510; 606/96; 607/1, 122
See application file for complete search history.

(56) References Cited

U.S. PATENT DOCUMENTS

| | | | |
|---|---|---|---|
| 5,341,807 A * | 8/1994 | Nardella | 600/381 |
| 5,810,888 A * | 9/1998 | Fenn | 607/154 |
| 6,023,638 A * | 2/2000 | Swanson | 600/510 |
| 6,188,355 B1 | 2/2001 | Gilboa | |
| 6,200,333 B1 | 3/2001 | Laufer et al. | |
| 6,226,543 B1 | 5/2001 | Gilboa et al. | |
| 6,245,065 B1 | 6/2001 | Panescu et al. | |
| 6,299,633 B1 | 10/2001 | Laufer et al. | |
| 6,380,732 B1 | 4/2002 | Gilboa | |
| 6,411,852 B1 | 6/2002 | Danek et al. | |
| 6,477,396 B1 | 11/2002 | Mest et al. | |
| 6,529,756 B1 | 3/2003 | Phan et al. | |

(Continued)

OTHER PUBLICATIONS

U.S. Appl. No. 60/625,256, filed Nov.5, 2004, Kaplan et al.

(Continued)

*Primary Examiner*—Carl H Layno
*Assistant Examiner*—Luther G Behringer
(74) *Attorney, Agent, or Firm*—Perkins Coie LLP

(57) ABSTRACT

Methods for treating a network of organs including generating a map of at least a portion of the network of organs using a rendering system; selecting at least one treatment location within the luminal passageway of the network of organs; and applying an energy therapy to the treatment location to treat the smooth muscle tissue, where the energy therapy applied to the respective treatment location is defined by a plurality of parameters that are associated with a map. Such a system allows for historical or ideal treatment parameters to be identified, visually or otherwise to actual treatment locations. Also, control systems and methods for delivery of energy that may include control algorithms that prevent energy delivery if a fault is detected and may provide energy delivery to produce a substantially constant temperature at a delivery site. In some embodiments, the control systems and methods may be used to control the delivery of energy, such as radiofrequency energy, to body tissue, such as lung tissue.

47 Claims, 9 Drawing Sheets

U.S. PATENT DOCUMENTS

| | | |
|---|---|---|
| 6,558,333 B2 | 5/2003 | Gilboa et al. |
| 6,574,498 B1 * | 6/2003 | Gilboa ........................ 600/424 |
| 6,575,969 B1 | 6/2003 | Rittman, III et al. |
| 6,593,884 B1 | 7/2003 | Gilboa et al. |
| 6,615,155 B2 | 9/2003 | Gilboa |
| 6,634,363 B1 | 10/2003 | Danek et al. |
| 6,662,034 B2 | 12/2003 | Segner et al. |
| 6,702,780 B1 | 3/2004 | Gilboa et al. |
| 6,711,429 B1 * | 3/2004 | Gilboa et al. ............... 600/407 |
| 6,833,814 B2 | 12/2004 | Gilboa et al. |
| 6,904,303 B2 | 6/2005 | Phan et al. |
| 6,926,669 B1 | 8/2005 | Stewart et al. |
| 6,947,788 B2 | 9/2005 | Gilboa et al. |
| 6,996,430 B1 | 2/2006 | Gilboa et al. |
| 7,027,869 B2 | 4/2006 | Danek et al. |
| 7,104,987 B2 | 9/2006 | Biggs et al. |
| 2003/0233099 A1 * | 12/2003 | Danaek et al. ................. 606/96 |
| 2003/0236455 A1 | 12/2003 | Swanson et al. |
| 2004/0031494 A1 | 2/2004 | Danek et al. |
| 2004/0138647 A1 * | 7/2004 | Osorio et al. ............ 604/890.1 |
| 2004/0167402 A1 * | 8/2004 | Jones et al. ................. 600/437 |
| 2004/0182399 A1 | 9/2004 | Danek et al. |
| 2005/0010270 A1 | 1/2005 | Laufer |
| 2006/0062808 A1 | 3/2006 | Laufer et al. |

OTHER PUBLICATIONS

U.S. Appl. No. 60/627,662, filed Nov. 12, 2004, Danek et al.
U.S. Appl. No. 60/650,368, filed Feb. 4, 2005, Kaplan et al.
U.S. Appl. No. 09/095,323, filed Jun. 10, 1998, Laufer.
U.S. Appl. No. 09/436,455, filed Nov. 8, 1999, Danek et al.

* cited by examiner

CONTROL SYSTEMS FOR DELIVERING ENERGY

CROSS-REFERENCE TO RELATED APPLICATIONS

This application claims the benefit under 35 U.S.C. §119 (e) of U.S. Provisional Application No. 60/673,876 filed Apr. 21, 2005, the contents of which are incorporated herein by reference.

BACKGROUND

Systems and devices exist for tracking a probe such as a catheter or endoscope through the body of a patient. Such systems and devices are described in U.S. Pat. No. 6,188,355 entitled Wireless six-degree-of-freedom locator; U.S. Pat. No. 6,226,543 entitled System and method of recording and displaying in context of an image a location of at least one point-of-interest in a body during an intra-body medical procedure; U.S. Pat. No. 6,380,732 entitled Six-degree of freedom tracking system having a passive transponder on the object being tracked; U.S. Pat. No. 6,558,333 entitled System and method of recording and displaying in context of an image a location of at least one point-of-interest in a body during an intra-body medical procedure; U.S. Pat. No. 6,574,498 entitled Linking of an intra-body tracking system to external reference coordinates; U.S. Pat. No. 6,593,884 entitled Intrabody navigation system for medical applications; U.S. Pat. No. 6,615,155 entitled Object tracking using a single sensor or a pair of sensors; U.S. Pat. No. 6,702,780 entitled Steering configuration for catheter with rigid distal device; U.S. Pat. No. 6,711,429 entitled System and method for determining the location of a catheter during an intra-body medical procedure; U.S. Pat. No. 6,833,814 entitled Intra-body navigation system for medical applications; and U.S. Pat. No. 6,996,430 entitled Method and system for displaying cross-sectional images of a body. Each of which is incorporated by reference in their entirety. each of which is incorporated by reference in their entirety.

In accordance with tracking devices as described above, novel medical procedures may require improved operator interface, beyond just positioning, to improve treatment results or outcome. The treatment of asthma is one such procedure. Devices and methods for treating airway walls are described in U.S. patent applications Nos.: Ser. No. 09/095,323 titled METHOD AND APPARATUS FOR TREATING SMOOTH MUSCLES IN THE WALLS OF BODY CONDUITS filed Jun. 10, 1998; Ser. No. 10/414,253 titled MODIFICATION OF AIRWAYS BY APPLICATION OF ENERGY filed Apr. 14, 2003; Ser. No. 09/436,455 titled DEVICES FOR MODIFICATION OF AIRWAYS BY TRANSFER OF ENERGY filed Nov. 08, 1999; Ser. No. 09/999,851 titled METHOD FOR TREATING AN ASTHMA ATTACK filed Oct. 25, 2001; Ser. No. 10/810,276 titled METHOD OF TREATING AIRWAYS IN THE LUNG filed Mar. 26, 2004; Ser. No. 10/640,967 titled METHODS OF TREATING ASTHMA filed Aug. 13, 2003; Ser. No. 10/809,991 titled METHODS OF TREATING REVERSIBLE OBSTRUCTIVE PULMONARY DISEASE filed Mar. 26, 2004; and Ser. No. 10/954,895 titled INACTIVATION OF SMOOTH MUSCLE TISSUE filed Sep. 30, 2004; and U.S. patents U.S. Pat. No. 6,411,852 titled CONTROL SYSTEM AND PROCESS FOR APPLICATION OF ENERGY TO AIRWAY WALLS AND OTHER MEDIUMS; and U.S. Pat. No. 6,634,363 titled DEVICES FOR MODIFICATION OF AIRWAYS BY TRANSFER OF ENERGY. Along with U.S. Provisional Application Ser. Nos.: 60/650,368 filed Feb. 04, 2005; 60/625,256 filed Nov. 05, 2004; and 60/627,662 filed Nov. 12, 2004. Each of the above patent applications, patents and provisional applications are incorporated by reference herein in their entirety.

Various obstructive airway diseases have some reversible component. Examples include COPD and asthma. Asthma is a disease in which bronchoconstriction excessive mucus production and inflammation and swelling of airways occur, causing widespread but variable airflow obstruction thereby making it difficult for the asthma sufferer to breathe. Asthma is a chronic disorder, primarily characterized by persistent airway inflammation. Asthma is further characterized by acute episodes of additional airway narrowing via contraction of hyper-responsive airway smooth muscle.

In susceptible individuals, asthma symptoms include recurrent episodes of shortness of breath (dyspnea), wheezing, chest tightness and cough. Currently, asthma is managed by a combination of stimulus avoidance and pharmacology. Stimulus avoidance is accomplished via systemic identification and minimization of contact with each type of stimuli. It may, however, be impractical and not always helpful to avoid all potential stimuli.

Pharmacological management of asthma includes long term control through the use of anti-inflammatories and long-acting bronchiodilators. Short term pharmacological management of acute exacerbations may be achieved with use of short-acting bronchiodilators. Both of these approaches require repeated and regular use of prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that trigger asthma are common barriers to successful conventional asthma management. Accordingly, it would be desirable to provide a management system and method that does not require regular patient compliance.

Various energy delivering systems have been developed to intraluminally treat anatomical structures by the controlled application of energy to intraluminal surfaces. Such systems may be specifically configured to deliver energy to lung tissue because of the clinical demands caused by the heterogeneous nature of lung tissue, and specifically, variations in lung tissue lumen size due to the branching pattern of the tracheobronchial tree, variations in the vasculature of the lungs and variations in the type of tissue in the lungs, including cartilage, airway smooth muscle, and mucus glands and ducts. Accordingly, a system designed to delivery energy, and in some particular cases, radiofrequency energy, to lung tissue must take these variations into account and deliver energy in a controlled manner.

Medical procedures involving the controlled delivery of therapeutic energy to patient tissue are often demanding and may require a physician to perform several tasks at the same time. In addition, medical procedures or other procedures may require specific energy delivery parameters. As such, what has been needed is an energy delivery system with a user friendly control system that regulates and controls the delivery of energy, prevents operation or energy delivery if a fault in the energy delivery system is detected by the control system and provides the user with information delivered in an easy to understand format so that the information can be readily analyzed during a demanding medical procedure.

In addition, there remains a need to combine the treatment systems described herein with a mapping system that to eventually enable the user to rely on safety measures as well as algorithms to enhance the procedure.

SUMMARY

It is noted that while the following disclosure discusses the treatment of asthma and the airways as one variation of the invention, the invention is not limited to such an indication. The invention may be applicable to nearly any medical treatment or therapy in which the association of information with treatment sites is useful.

In one embodiment of the invention, the invention includes a method for treating a network of organs, such as the airways which have smooth muscle tissue surrounding the airway luminal passageway, the method comprising, generating a map of at least a portion of the network of organs using a rendering system; selecting at least one treatment location within the luminal passageway of the network of organs; and applying an energy therapy to the treatment location to treat the smooth muscle tissue, where the energy therapy applied to the respective treatment location is defined by a plurality of parameters. These parameters may include but are not limited to time of treatment, time between treatments, temperature, energy, rate of change in temperature, rate of change in energy, impedance of the treatment location, and a combination thereof. The parameters may be displayed during or subsequent to the treatment.

The term luminal passageway may include the cavity of a tubular or other organ such as the airways, esophagus, gastrointestinal tract, vasculature, heart, kidneys, liver, bladder, and/or brain, or it may also refer to a non-naturally occurring cavity created in the tissue of an organ.

The map may be a virtual map or compiled map that is generated by a computer aided tomography (CT), magnetic resonance imaging (MRI), positron emission tomography (PET), ultrasonic imaging, or other similar rendering system in which the desired anatomy may be essentially mapped through the compilation of various images or data. It should be noted that the map or virtual map may simply be a graphical representation of the movement of the device within the body relative to a particular reference point. The map may also be purely a series of coordinates relative to a fixed reference point somewhere in the body. Such a map is useful to identify the location of a device in the organs even though the map is not represented in a graphic image. It may also be used to display the location of the device as compared to the locations that have already been visited, diagnosed, or treated by the device.

Once the map is generated, it may be useful to orient the constructed map with anatomical features or locations within the body. Such orientation permits correlation of positions on the map with actual movement of the device within the body. The map may be generated prior to beginning the actual treatment. For example, a patient may undergo a CT scan to generate the images necessary for construction of the map. Once completed, the medical procedure may be initiated with a complete or substantially complete map.

Although it may be useful to display the map on a visual display, such as the visual display of an image provided by a scope-type device, the map may be displayed on a separate monitor apart from the visual display. The monitor may provide a graphical illustration or representation of the network of organs and/or may merely provide positioning data.

As noted above, the invention may combine some type of locating system and locating implement to track the position of the device within the network of organs (where the term device includes catheters, access devices, probes, or other such items). In one example, the locating implement and locating system described in the patents referenced above may be incorporated in the treatment device or in a separate device. However, variations of the invention may use other locating systems such as RFID systems. In any case, the locating implement will communicate with the locating system to establish a virtual position of the device on the map. Accordingly, the virtual position may then be imposed on the real time image of the luminal passageways on a visual display.

The system of the present invention may also generate a diagnostic or treatment history profile where the diagnostic or treatment history profile includes the virtual position of the device at each diagnosis point or treatment location when applying the energy therapy. It should be noted that the treatment may be applied in one step (such as exposing the body to a single source of energy (from within or outside the body.) Alternatively, sections of the organ may be treated with in stages (for example, when the organ is treated in stages to alleviate the healing load on the organ, to minimize the patient's time under sedation, etc.).

Control System

With regards to the control system, in one embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a visual indicator is coupled to the energy generator and the processor is configured to activate the visual indicator when a temperature measured by the temperature detecting element is not within a pre-determined temperature range.

In another embodiment, an energy delivery system includes a therapeutic energy delivery device having a distal portion configured to be delivered to a treatment site. The distal portion includes a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a visual indicator is configured to activate the visual indicator when a temperature measured by the temperature detecting element is not within a pre-determined temperature range.

In another embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a visual indicator is configured to activate the visual indicator when an impedance of an energy emission circuit between the energy generator, the energy emission element and a patient is not within a predetermined impedance range.

In another embodiment, an energy delivery system includes a therapeutic energy delivery device having a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a visual indicator is configured to activate the visual indicator when an impedance of an energy emission circuit between the energy generator, the energy emission element and a patient is not within a pre-determined impedance range.

In yet another embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a first visual indicator and a second visual indicator, is configured to activate the first visual indicator when a temperature measured by the temperature detecting element is not within a pre-determined temperature range and to activate the second visual indicator when an impedance of an energy emission circuit between the energy generator, the energy emission element and a patient is not within a pre-determined impedance range.

In another embodiment, an energy delivery system includes a therapeutic energy delivery device configured to be delivered to a treatment site. The energy delivery device has a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a first visual indicator and a second visual indicator is configured to activate the first visual indicator when a temperature measured by the temperature detecting element is not within a pre-determined temperature range and to activate the second visual indicator when an impedance of an energy emission circuit between the energy generator, the energy emission element and a patient is not within a pre-determined impedance range.

In another embodiment, an energy delivery system includes a therapeutic energy delivery catheter having an electrode and temperature detecting element disposed on a distal portion of the catheter. The distal portion of the catheter is configured to be delivered to a treatment site adjacent target tissue of a patient and deliver a treatment cycle of therapeutic RF energy to the target tissue. An RF energy generator is configured to be coupled to the electrode and has an activation state and a standby state, where RF energy is delivered to and emitted from the electrode in the activation state and not in the standby state. A controller having a processor and a user interface surface with a first visual indicator and second visual indicator is configured to process temperature measurements taken by the temperature detecting element and impedance measurements between the RF energy generator and the target tissue prior to activation of the RF energy generator to the activation state. The processor is also configured to activate the first visual indicator if a temperature measured by the temperature detecting element is not within a pre-determined temperature range and activate the second visual indicator when an impedance between the RF energy generator and target tissue adjacent the electrode is above a predetermined value.

These features of embodiments will become more apparent from the following detailed description when taken in conjunction with the accompanying exemplary drawings.

DETAILED DESCRIPTION

Embodiments of systems and methods for delivering energy to tissue of a patient in a controlled manner are discussed, and specifically, systems and methods for controlled delivery of radiofrequency (RF) energy to lung tissue, bronchial tissue or both. However, the present systems and method may include various other types of energy delivery modes that achieve the intended treatment of tissue. During the procedure, the medical practitioner applies therapy to the treatment locations where the energy applied to the respective treatment location is defined by a number of parameters. Recordation of these parameters and association of the parameters with the treatment site may be important for a number of reasons, including follow-up evaluation, further treatment, or to avoid excessive treating of an area.

Embodiments of the systems and methods may be configured to consolidate and effectively communicate relevant information to a user of the systems, including detecting accessory (e.g. therapeutic device, footswitch, electrode return pad, or other) connections and serving as an automatic trouble shooting guide with user friendly instructions, information, indicators and the like.

Figure 1:
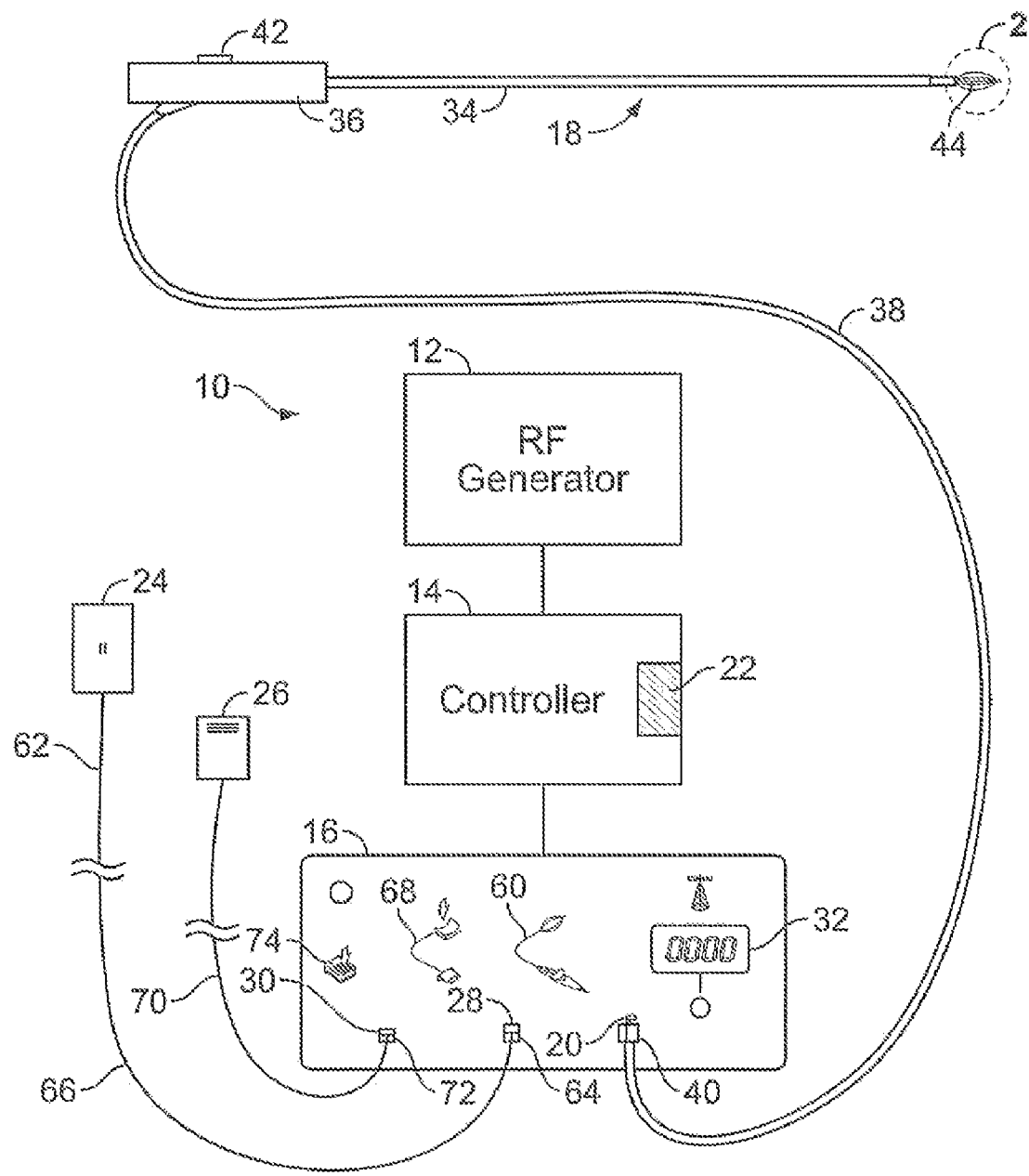
FIG. 1 is a schematic view of a system for delivering energy to the wall tissue of a patient's lung.

FIG. 1 shows a schematic diagram of a system for delivering therapeutic energy 10 to tissue of a patient having an RF energy generator 12, a controller 14 coupled to the energy generator, a user interface surface 16 in communication with the controller 14 and a therapeutic energy delivery device, in the form of an RF energy delivery device 18, coupled to an interface coupler 20 on the user interface surface 16. The controller 14, which is coupled to the energy generator 12 and user interface surface 16, is configured to control the energy output of the energy generator 12. The user interface surface 16 may include switches, a digital display, visual indicators, graphical representations of components of the system and an audio tone generator as well as other features. The controller 14 includes a processor 22 that is generally configured to accept information from the system and system components, and process the information according to various algorithms to produce control signals for controlling the energy generator 12. The processor 22 may also accept information from the system 10 and system components, process the information according to various algorithms and produce information signals that may be directed to the visual indicators, digital display or audio tone generator of the user interface in order to inform the user of the system status, component status, procedure status or any other useful information that is being monitored by the system. The processor 22 of the controller 14 may be digital IC processor, analog processor or any other suitable logic or control system that carries out the control algorithms. Some of the control alerts, information, feedback and testing routines are shown in the flow diagram of FIGS. 5A and 5B.

The system 10 also includes an electrode return pad 24 and a footswitch 26, both of which are coupled to respective interface couplers 28 and 30 on the user interface surface 16. The user interface surface 16 also includes a digital display 32 that may be used to display numeric data to a user of the system 10. The arrangement of the user interface surface 16 provides a user friendly interface for the system 10 that provides feedback and system information to a user in an intuitive display format. System components that couple to the user interface surface 16, such as the footswitch 26, electrode return conductive pad 24 and energy delivery device 18, couple to the user interface surface 16 adjacent graphical representations of the respective system components. In addition, visual indicators that are configured to display information about these various system components may also be disposed adjacent or within the respective graphical representation of each system component. This configuration allows a user to easily and intuitively couple system components to the proper interface on the user interface surface 16 and also allows a user to easily and intuitively correlate audio and visual system feedback to the appropriate system component.

Referring again to FIG. 1, the energy delivery device 18 includes an elongate shaft 34, a handle 36 secured to a proximal end of the elongate shaft 34 and a control cable 38 that extends from the handle 36 to a proximal coupler 40 that is configured to couple to the interface coupler 20 on the user interface surface 16. A sliding switch 42 on the handle 36 controls the radial expansion and contraction of a distal electrode basket 44 disposed on a distal end of the elongate shaft 34. The elongate shaft 34 may have a variety of configurations, including stiff, flexible, steerable with distal tip deflection and the like. The elongate shaft 34 and distal portion may also be configured and sized to permit passage of the elongate shaft 34 through the working lumen of a commercially available bronchoscope. In addition, the controller 14 may also include an optional interface coupler (not shown) that is configured to couple to a bronchoscope camera trigger such that when the processor 22 of the controller 14 initiates a treatment cycle by switching the RF energy generator from a standby state to an activation state, a triggering signal is also generated by the controller to initiate video taping or displaying of an image produced by the bronchoscope camera which is coupled to a bronchoscope being used to position the energy delivery device 18 during a procedure or treatment cycle. Alternatively, the controller may utilize the interface coupler to send some or all of the controller output to the bronchoscope video processor or monitor. In this way, the information displayed on the controller's user interface surface can also be displayed on any of the displays associated with the bronchoscope. Additionally, controller output information that is not displayed on the controller's user interface surface can be displayed on any of the displays associated with the bronchoscope. This may be of use, because the physician is typically focused on the bronchoscope display when conducting a procedure.

Figure 2:
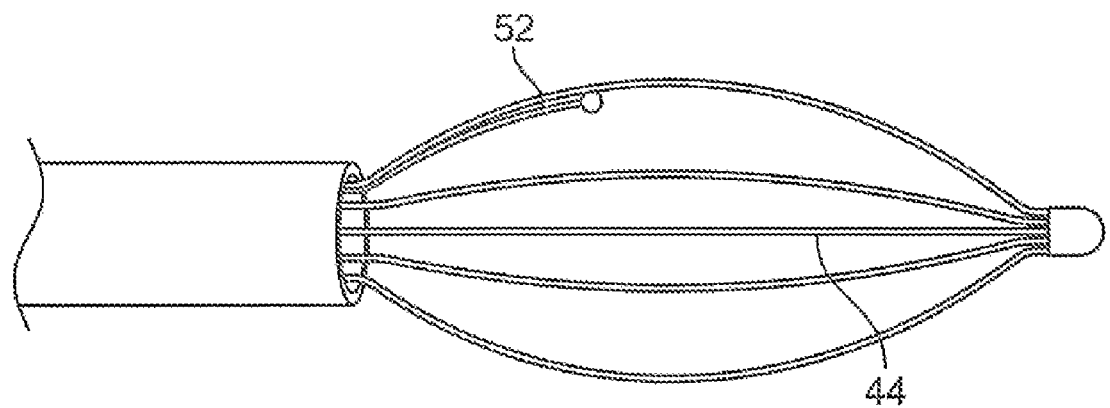
FIG. 2 is an enlarged view of a distal portion of a therapeutic energy delivery device.
Figure 3:
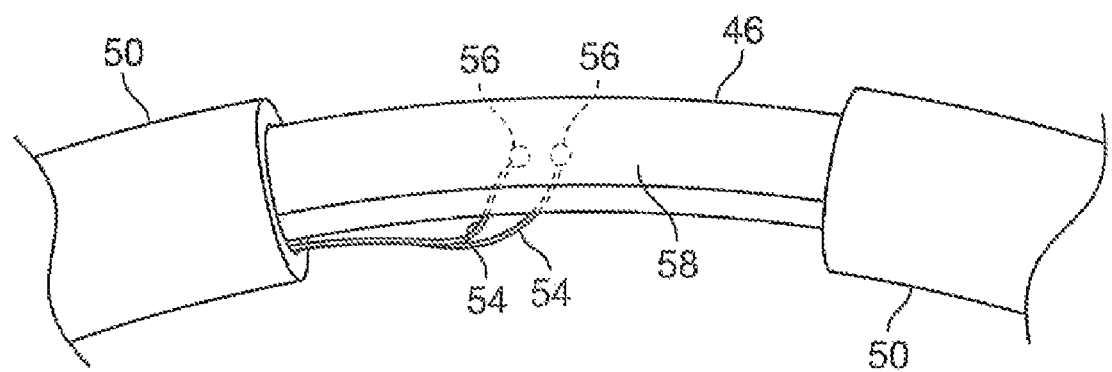
FIG. 3 is an enlarged view of a portion of FIG. 2 illustrating a more detailed view of an energy emission element and temperature detecting element of the therapeutic energy delivery device.

The distal electrode basket 44 may be seen in more detail in FIGS. 2 and 3. The distal electrode basket 44 is a flexible and resilient oval shaped basket that includes an energy emission element in the form of an electrode 46 that is formed from an exposed section of a basket leg 48 which is nominally coated with an electrical insulator material 50 in the areas outside of the exposed section. The distal electrode basket 44 also includes a temperature detection element in the form of a thermocouple 52 disposed on or adjacent the electrode 46. The thermocouple 52 has leads 54 and thermocouple termination points 56 which are secured to the exposed section 58 of the basket leg or electrode 46.

The leads 54 of the thermocouple 52 and a conductor (not shown) in electrical communication with the electrode 46 extend proximally from the distal basket 44 to the handle 36 and then proximally through the control cable 38 to the proximal coupler 40. This configuration allows the electrode 46 and the thermocouple leads 54 to be electrically coupled in a modular arrangement with the controller 14 through the user interface surface 16. The interface coupler 20 configured to accept the proximal coupler 40 of the energy delivery device 18 is disposed adjacent a graphical representation 60 of an embodiment of the energy delivery device 18 which is printed on the user interface surface 16. This provides a useful visual prompt for a user who is setting up the system 10. Once the proximal coupler 40 is connected to the interface coupler 20 for the energy delivery device 18, the electrode 46 is now in electrical communication with the RF energy generator 12, subject to control and modulation by the controller 14 which may switch the RF generator 12 back and forth between an active state and a standby state, during which no RF can be delivered. In addition, the leads 54 of the thermocouple 52 are also in electrical communication with the controller 14 so that the controller 14 may monitor the temperature of the tissue adjacent the electrode 46. In this arrangement, the RF energy generator 12, controller 14 and user interface 16 form a system for controlled delivery of activation energy to the energy delivery device 18.

The electrode 46 may be monopolar or bipolar, however, if the electrode 46 is a monopolar electrode, a return electrode component 62 may be used with the system 10 in order to complete an electrical energy emission or patient circuit between the RF energy generator 12 and a patient (not shown). The electrode return 62 includes the conductive pad 24, a proximal coupler 64 and a conductive cable 66 extending between and in electrical communication with the conductive pad 24 and proximal coupler 64. The conductive pad 24 may have a conductive adhesive surface configured to removably stick to the skin of a patient and with a large enough surface area such that no burning or other injury to the patient's skin will occur in the vicinity of the conductive pad 24 while the system 10 is in use. The proximal coupler 64 is configured to couple to the interface coupler 28 on the user interface surface 16. The interface coupler 28 for the electrode return 62 is disposed adjacent a graphical representation 68 of the electrode return 62 on the user interface surface 16. Once again, this provides a useful visual prompt for a user who is setting up the system 10.

Once the proximal coupler 40 of the energy delivery device 18 and the proximal coupler 64 of the electrode return 62 have been coupled to the controller 14 via the respective interface couplers 20 and 28 of the user interface surface 16, RF energy may be generated by the RF generator 12, i.e., the RF generator 12 is switched to an activation state, and emitted from the electrode 46 of the distal basket 44 of the energy delivery device 18 into target tissue of the patient adjacent the electrode 46. The processor 22 may then adjust the output of the RF generator 12 in order to maintain a substantially constant temperature of tissue adjacent the electrode via a feedback loop between the thermocouple 52 and the processor 22. The processor 22 may use a control algorithm to process the temperature feedback and generate control signals for the RF generator 12. In addition, control algorithm may be configured to set predetermined dwell or activation times for embodiments of treatment cycles. Embodiments of control algorithms and system components that may be used in conjunction with control device and method embodiments discussed herein may be found in U.S. patent application Ser. No. 10/414,411, titled "Control System and Process for Application of Energy to Airway Walls and Other Mediums", filed Apr. 14, 2003, which is incorporated by reference herein in its entirety.

In one embodiment, the RF generator 12 generates RF energy at a frequency of about 400 kHz to about 500 kHz in with a wattage output sufficient to maintain a target tissue temperature of about 60 degrees C. to about 80 degrees C., specifically, about 60 degrees C. to about 70 degrees C. The duration of the activation state for an embodiment of a single treatment cycle may be about 5 seconds to about 15 seconds, specifically, about 8 seconds to about 12 seconds. Alternatively, the duration of the activation state of the RF generator may also be set to not more than the duration required to deliver about 150 Joules of energy to the target tissue, specifically, not more than the duration required to deliver about 125 Joules of RF energy to target tissue.

Figure 4:
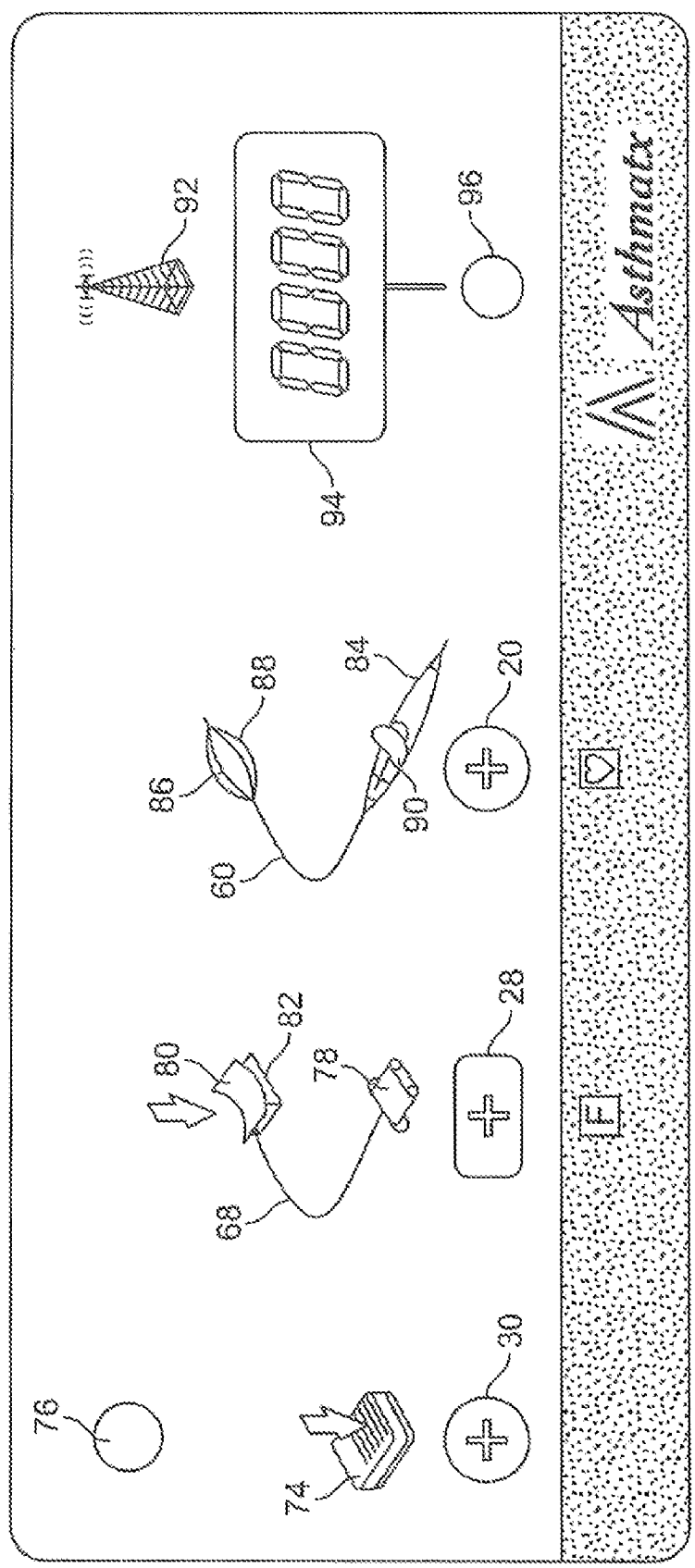
FIG. 4 is an elevational view of a user interface surface of a controller.

The initiation of the activation state of the RF generator 12 may be carried out by a variety of devices and methods, however, the embodiment of FIG. 1 includes a user operated activation switch in the form the footswitch 26. A conductive cable 70 is coupled to and disposed between the footswitch 26 and a proximal coupler 72 which is configured to be electrically coupled to the respective interface coupler 30 disposed on the user interface surface 16. The interface coupler 30 for the proximal coupler 72 of the footswitch 26 is disposed adjacent a graphical representation 74 of the footswitch 26 on the user interface surface 16. The footswitch 26 may be used in some configurations to initiate an activation state of the RF energy generator 12 if all components of the system 10 are functioning and connected properly. This can be defined as the controller entering into the ready mode Referring now to FIG. 4, a more detailed view of an embodiment of the user interface surface 16 is shown. The user interface surface 16 may be a substantially rectangular and flat surface as shown in FIG. 4, but may also have any other suitable shape, size or configuration. The user interface surface 16 may, in some embodiments, be any part of an energy delivery system, or component thereof, that a user may access or see in order to impart information or receive information therefrom. The controller 14 may have an alternating current (AC) power on/off switch that may be located anywhere on the controller 14, or alternatively, on the user interface surface 16. However, for the embodiment shown in FIG. 4, the user interface surface 16 does not include an AC power on/off switch. The controller 14 or user interface surface 16 may include an audio tone generator (not shown) which may be used in conjunction with the various visual indicators of the system 10 to alert a user to the status of the various components of the system 10. In one embodiment, the audio tone generator includes a speaker (not shown) which may be mounted on any suitable surface of the controller 12 or the user interface surface 16.

The user interface surface 16 has a visual indicator in the form of a multi-colored LED ready indicator light 76 in the upper left hand corner of the user interface surface 16. The ready indicator light 76 may be activated or lit with a first color, such as a green color, when the RF energy generator 12 is ready for use in a standby state. The LED indicator 76, may be activated and lit with a second color, such as an amber color, when the RF energy generator 12 is switched on into an activation state at which time a brief audio tone may also sound upon the transition of the RF generator 12 from the standby or ready state to the activation state with RF energy being delivered to the energy emission element 46 of the energy delivery device 18. Additionally, a separate LED indicator 92 may be activated and lit with a second color, such as a blue color, during RF energy delivery. Typically, a user activates the RF energy generator 12 for a treatment cycle by depressing and releasing the footswitch 26. The color of the ready indicator light 76 may be switched back to the first color if, during an activation cycle, the footswitch 26 of the system 10 is depressed and released again so as to produce a footswitch shutoff response from the processor 22 which switches the RF energy generator 12 from the activation state to the standby state. The second color or amber color may also be displayed by the ready indicator light 76 when the system 10 is engaged in a power on self-test (POST) mode during which time the audio tone generator may be delivering a constant single pitch tone. In addition, the second amber color may also be displayed by the ready indicator when a fault with the energy delivery device 18, such as a broken electrode 46 or broken thermocouple 52, is detected by the controller 14. The activation of the second color indicating a fault with the energy delivery device 18 may also be accompanied by an audible first error tone from the audio tone generator. The ready indicator light 76 may flash the first color, green, when the system 10 is conducting a cycling of the AC power to the controller 14 in order to reset the system 10 during which time the audible first error tone may also be produced. In essence, the ready indicator light 76 emits a first color when the system 10 is ready to use and a second color or amber color if the system 10 has detected a fault in the system 10 and is not ready to use.

Below the LED ready indicator 76 is the graphical representation 74 of the footswitch 26 which is printed on the user interface surface 16. The graphical representation 74 of the footswitch 26 is directly above and adjacent to the interface coupler 30 which is configured to accept the proximal coupler 72 of the footswitch 26 assembly. The graphical representation 74 of the footswitch 26 adjacent the interface coupler 30 for the footswitch 26 provides an intuitive and user friendly prompt for the user to locate the plug in point for the footswitch 26 while setting up the system 10.

To the right of the graphical representation 74 of the footswitch 26 is the graphical representation 68 of the electrode return assembly 62 which includes the conductive pad 24, conductive cable 66 and proximal coupler 64 and which is printed on the user interface surface 16. The graphical representation 78 of the proximal coupler 64 of the electrode return assembly 62 is disposed directly above and adjacent to the interface coupler 28 for the proximal coupler 64 of the electrode return assembly 62. A visual indicator in the form of an amber colored LED light 80 is disposed within the graphical representation 82 of the conductive pad 24 of the electrode return assembly 62 and on the user interface surface 16. The visual indicator 80 may be configured to be lighted in a steady state when the system 10 is proceeding through the POST which may also be accompanied by a single pitch audible tone from the audio tone generator. The visual indicator 80 may also be activated and lighted when the controller 14 measures an impedance in the patient circuit that is above a predetermined value after 3 or more attempts to activate the RF energy generator to the activation state. A second error tone may accompany the activation of the visual indicator in this circumstance. For some embodiments, the predetermined impedance value for the patient circuit may be above about 1000 Ohms, specifically, above about 900 Ohms. Such a high impedance measurement in the patient circuit indicates an open circuit and requires that the user check the patient circuit and try the system 10 another time. The patient circuit includes the electrode 46 and conductive cable 38 of the energy delivery device 18, the patient (not shown) with the conductive pad 24 and electrode 46 in electrical communication with the patient's body, and the electrode return assembly 62, The visual indicator 80 may also be activated or lighted in a flashing mode when a fault requiring the user to cycle AC power has been initiated by the processor 22, during which time a first audible error tone may also be generated by the audio tone generator.

To the right of the graphical representation 68 of the electrode return 62, the graphical representation 60 of the energy delivery device 18 is printed on the user interface surface 16 including the handle 36, the elongate shaft 34 and the distal electrode basket 44. The interface coupler 20 configured to accept the proximal coupler 40 of the energy delivery device 18 is disposed adjacent and directly below a graphical representation 84 of the handle 36 of the energy delivery device 18. A first visual indicator in the form of an amber LED light 86 is disposed within the graphical representation 88 of the distal electrode basket 44 on the user interface surface 16. A second visual indicator 90, having a second color different from the first visual indicator, in the form of a red LED light 90 is disposed within the graphical representation 84 of the handle 36.

The first visual indicator 86 may be activated and lighted for some embodiments of the system 10 when the controller 14 measures an impedance in the patient circuit that is above a predetermined value. For some embodiments, the predetermined impedance value for the patient circuit may be above about 1000 Ohms, specifically, above about 900 Ohms. A first audible error tone may also be generated during such an activation. The first visual indicator 86 may also be lighted or activated when the measured impedance of the patient circuit is above such a predetermined value during at least 3 or more attempts to activate the RF energy generator 12 to the activation state. In this circumstance, a second audible error tone may also be generated in conjunction with the activation of the first visual indicator 86. The first visual indicator 86 may also be lighted in a steady state when the processor 22 of the system 10 is proceeding through the POST which may also be accompanied by a single pitch audible tone from the audio tone generator. The visual indicator 86 may also be activated or lighted in a flashing mode when a fault requiring the user to cycle AC power has been initiated by the processor 22, during which time a first audible error tone may also be generated by the audio tone generator.

The second visual indicator 90 may be activated or lighted in a flashing or intermittent mode when a fault with the energy delivery device 18, such as a broken electrode 46 or broken thermocouple 52, is detected by the controller 14. The activation of the second visual indicator 90 suggesting a fault with the energy delivery device 18 may also be accompanied by an audible first error tone from the audio tone generator. The second visual indicator 90 may also be lighted in a steady state when the processor 22 of the system 10 is proceeding through the POST which may also be accompanied by a single pitch audible tone from the audio tone generator. The second visual indicator 90 may also be activated or lighted in a flashing mode when a fault requiring the user to cycle AC power has been initiated by the processor 22, during which time a first audible error tone may also be generated by the audio tone generator.

Another visual indicator 92 in the form of a graphical representation of a radiating electrode is disposed on the user interface surface 16. This RF energy indicator 92, which may be a third color or blue LED, is activated or lighted in a flashing mode during the time when the RF energy generator 12 is switched to the activation state and delivering RF energy to the energy delivery device 18. The RF energy indicator 92 may also be lighted in a steady state when the processor 22 of the system 10 is proceeding through the POST which may also be accompanied by a single pitch audible tone from the audio tone generator. The RF energy indicator 92 may also be activated or lighted in a flashing mode when a fault requiring the user to cycle AC power has been initiated by the processor 22, during which time a first audible error tone may also be generated by the audio tone generator.

A digital display 94 is disposed on the user interface surface 16 below the RF energy indicator 92 and is configured to display numerical information. The digital display 94 may be controlled or otherwise reset by a switch 96 disposed directly below the digital display 94 on the user interface surface 16. In a normal mode, the digital display 94 will display the number of successful treatment cycles delivered by the system 10 performed by a user of the system 10. If the switch 96 is depressed for less than about 2 seconds to about 4 seconds, the number of unsuccessful or incomplete treatment cycles is displayed for a brief period, such as about 5 seconds. After this brief period, the digital display 94 reverts back to a display of the number of completed treatment cycles. When the switch 96 is depressed and held for more than a brief period of about 2 seconds to about 4 seconds, the digital display 94 shows a "0" for a short period, such as about 1 second. If the switch 96 is held depressed during this short 1 second period, the count of the complete and incomplete treatment cycles is reset to 0. If the switch 96 is released during this short 1 second period, the digital display 94 reverts back to a display of the completed or successful treatment cycles without resetting the treatment cycle counter.

Figure 5A:
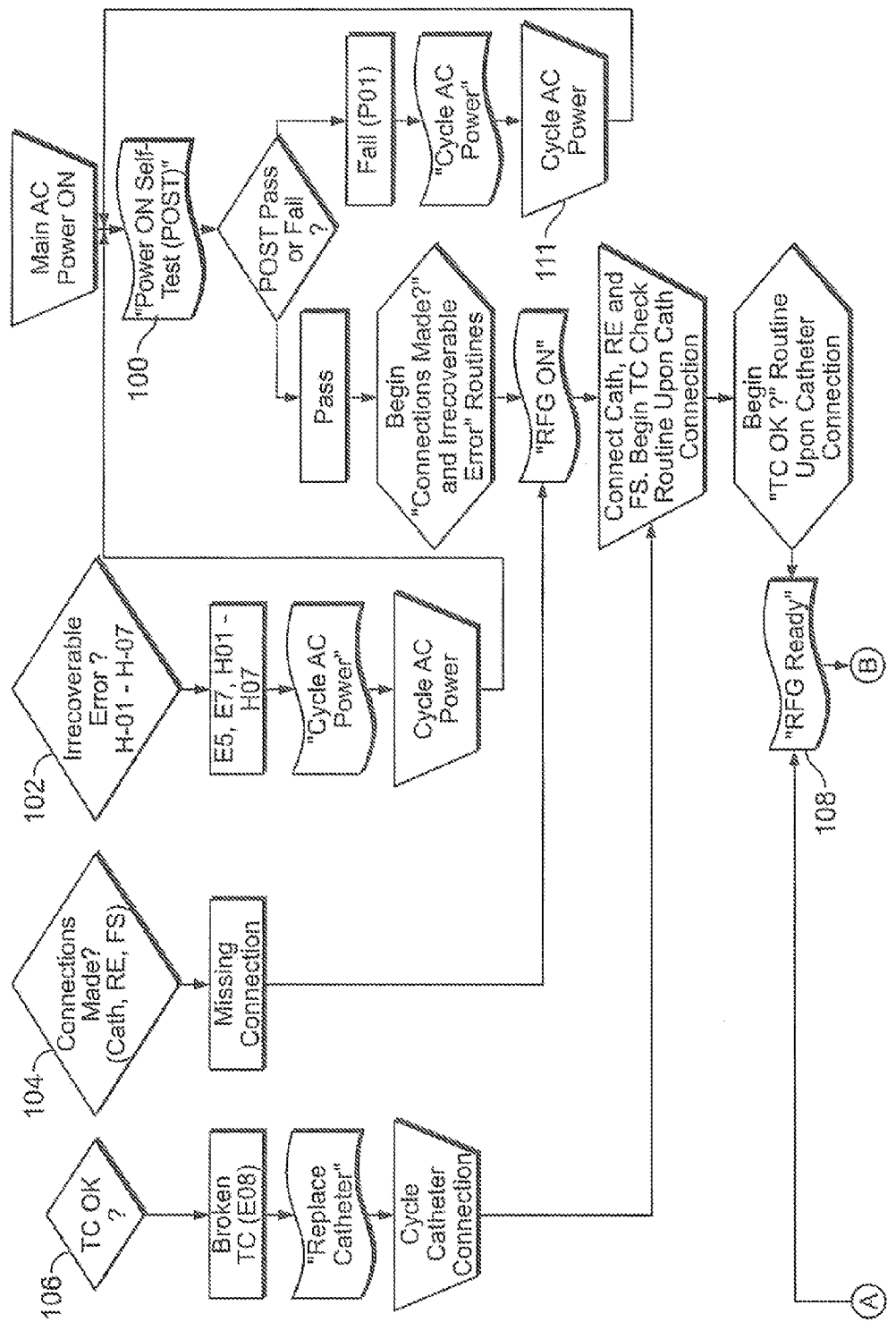
FIGS. 5A and 5B are flow diagrams depicting various processes and routines that control the user interface surface elements.
Figure 5B:
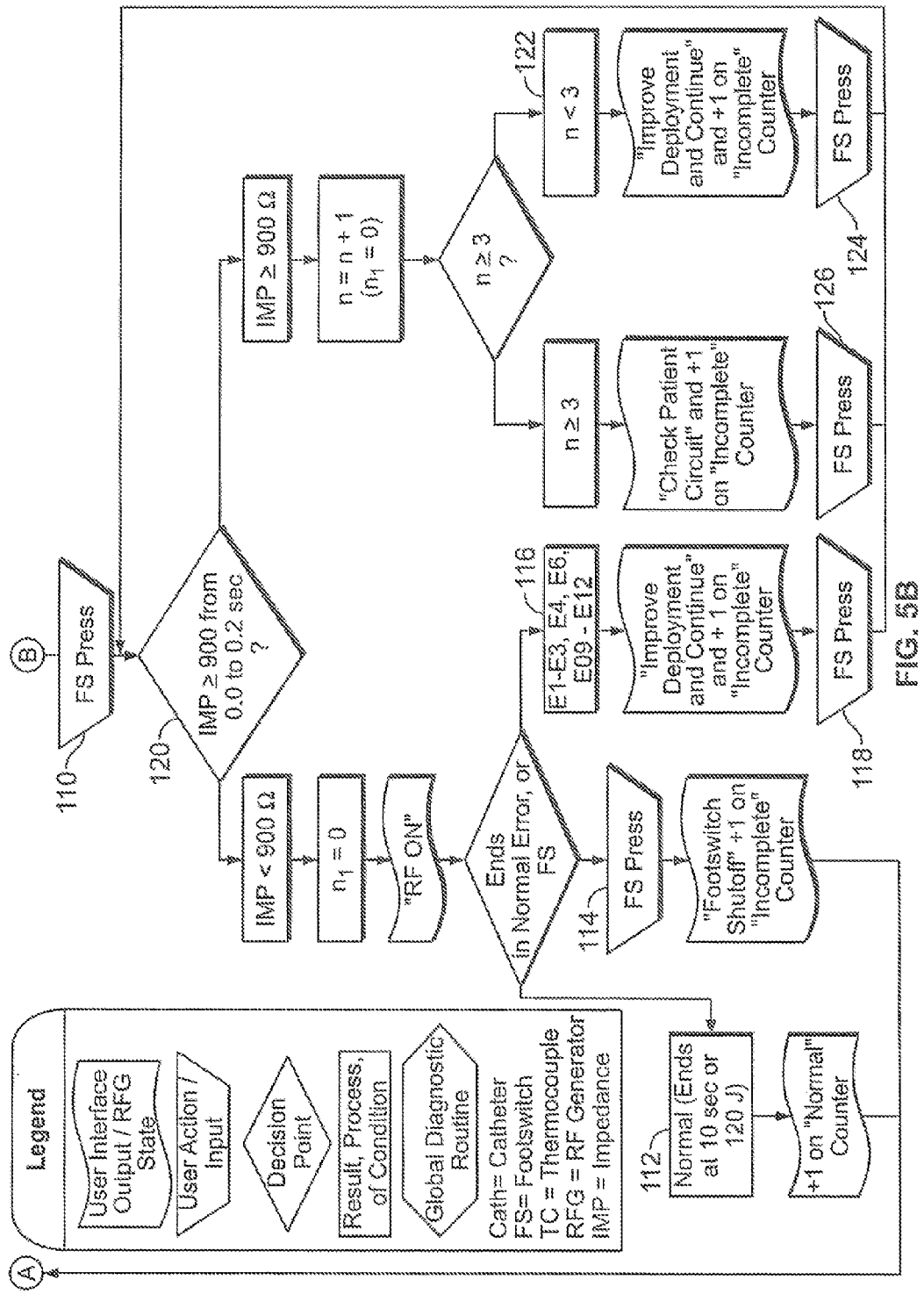

Referring to FIGS. 5A and 5B, a variety of system process embodiments are shown in flow diagram form. In use, the system 10 for delivery of therapeutic energy is first supplied with power, such as AC power, which may be carried out by a switch (not shown) on the controller 14 or user interface surface 16, as discussed above. Once AC power is supplied to the controller 14, the user initiates the POST cycle, indicated by box 100, which tests the integrity of the processor 22, the controller 14 and the system 10 generally. If the POST fails, the processor 22 initiates a cycling of the AC power in order to reboot the controller 14, and specifically, the processor 22 of the controller 14. In addition, once AC power has been supplied to the controller 14, the processor 22 continually runs a first background algorithm, indicated by the decision point "irrecoverable error" 102. The irrecoverable error test checks for hardware and processor errors such as CPU configuration, COP timeout, ROM CRC error, RAM, illegal CPU instruction, software, non-volatile memory, RF current measurement errors. If such an error is detected, the user should initiate a cycling of the AC power, as indicated by box 111, in order to reboot the controller 14, and specifically, the processor 22 of the controller 14. During the cycling of the AC power, the user will be informed of the cycling status by a flashing of all visual indicators on the user interface surface 16 as well as a flashing of the digital display 94 and the concurrent generation of an audible error tone.

If the POST is successful, the processor 22 will initiate a test algorithm that determines whether all connections of system components, such as the energy delivery device 18, return electrode 62 and footswitch 26 are all properly coupled to the respective interface couplers 20, 28 and 30 of the user interface surface 16, as indicated by decision point 104. If an error is detected during this routine, the ready indicator light 76 will remain in the second or amber color state, indicating that the RF energy generator 12 is not ready or in the standby state. Once the system components such as the energy delivery device 18, electrode return 62 and footswitch 26 are properly coupled to the user interface 16, the processor 22 will initiate an algorithm that determines whether the temperature detection element, or thermocouple 52, of the energy delivery device 18 is properly functioning as indicated by box 106.

During this test, the processor 22 measures the temperature indicated by the thermocouple 52 and compares the result to a predetermined temperature range, that encompasses room temperature for some embodiments. For example, the predetermined temperature range for some embodiments may be about 15 degrees C. to about 35 degrees C., specifically, about 20 degrees C. to about 30 degrees C. If the measured temperature indicated by the thermocouple 52 does not fall within the predetermined temperature range, the processor 22 indicates a broken thermocouple 52 by initiating an error message to the user which includes switching the ready indicator light 76 to the second or amber color in addition to initiating a flashing mode activation of the red LED second visual indicator 90 in the handle 84 of the graphical representation 60 of the energy delivery device 18. An audible error tone may also accompany the error message generated by the visual indicators 76 and 90. These error messages inform the user that it may be necessary to replace the energy delivery device 18 with a new one.

Once the thermocouple test has been successfully performed, the processor 22 will switch the ready indicator light 76 to the first color or green color indicating that the system 10 is now ready to perform a treatment cycle in a patient, as indicated by box 108. At this point, the user may then position the distal electrode basket 44 of the energy delivery device 18 such that at least one emission element or electrode 46 is disposed adjacent target tissue of the patient, such as smooth muscle of the patient's bronchial airways. Once the electrode 46 is properly positioned, the user depresses the footswitch 26 to initiate a treatment cycle, as indicated by user action/input box 110. Upon depression of the footswitch 26, the processor 22 immediately measures the impedance of the patient circuit, and if the impedance is below a predetermined maximum or within a predetermined impedance range, the processor 22 switches the RF energy generator 12 from the ready or standby state to the activation state wherein RF energy is being delivered to the target tissue of the patient for the initiation of a treatment cycle.

For some embodiments of a normal treatment cycle, as indicated by result box 112, the processor 22 and algorithms run by the processor 22 are configured to maintain the RF energy generator 12 in the activation state for a dwell time of about 5 seconds to about 15 seconds, specifically, about 8 seconds to about 12 seconds. The duration of the treatment cycle may also be constrained by the total energy delivered to the target tissue during the cycle. For example, the processor 22 may execute an algorithm which terminates the treatment cycle when the total energy delivered to the target tissue is up to about 150 Joules, specifically, up to about 125 Joules. During the treatment cycle, the processor 22 controls the output of the RF energy generator 12 in order to maintain a substantially constant temperature of the target tissue. The temperature of the target tissue during a treatment cycle embodiment may be maintained at a temperature of about 60 degrees C. to about 80 degrees C., specifically, from about 60 degrees C. to about 70 degrees C. As discussed above, the processor 22 is able to maintain the substantially constant temperature of the target tissue by monitoring the temperature of the target tissue via the temperature measuring element or thermocouple 52 and processing the temperature information in a feedback loop with lowers the RF energy generator 12 output if the measured temperature is higher than desired and increasing the RF energy generator output if the measured temperature is lower than desired.

During the treatment cycle, the processor 22 will switch the blue RF energy visual indicator 92 to an activated solid, or flashing mode and will activate the audio signal generator to generate a dual pitch audible tone from the audible tone generator that repeats a high pitch then low pitch audible tone during the treatment cycle, followed by a long single pitch tone at the end of a successful cycle. If an error occurs in the middle of a treatment cycle, an audible error tone will be generated and the visual indicator or indicators indicative of the error will be activated as discussed above. As discussed above, a treatment cycle may also be interrupted by the user's depression of the footswitch 26 during the treatment cycle to initiate a footswitch shutoff, as indicated by user action box 114. This may be done if the user feels that the system 10 is operating improperly for any reason, the user feels that the location of the electrode 46 is wrong, or for any other reason. A footswitch shutoff action by the user returns the system 10 to the RF generator ready state, indicated by box 108, but does not log a completed or successful treatment cycle on the digital display 94. If the treatment cycle is successfully completed, the digital display 94 will display a count of "1", indicating one successfully completed treatment cycle.

If an error occurs during the treatment cycle, as indicated by result box 116, or the footswitch shutoff option is used, a "0" will remain displayed. However, if the display control switch 96 is depressed for more than about 2 seconds to about 4 seconds, the digital display 94 will show a "1", indicating one incomplete or unsuccessful treatment cycle. The user may continue to deploy the energy delivery device 18 to new locations within the patient's anatomy and activate the RF energy generator 12 to the activation state for any desired number of treatment cycles. If an error occurs during a treatment cycle, as indicated by result box 116, the user interface 16 will then display via the appropriate visual indicators and audible tone indicators, the type of error that has occurred and will recommend a course of action for the user. After correction has been attempted by the user, the footswitch 26 may again be depressed, as indicated by user action/input box 118, in order to initiate another treatment cycle.

If the impedance of the patient circuit is greater than a predetermined maximum or not within a predetermined impedance range upon depression of the footswitch 26, as indicated by result box 120, one of two error messages including visual indicators and audible tones may be generated by the system 10. Specifically, if a high impedance is measured upon a first depression of the footswitch 26 or a second depression of the footswitch 26, as indicated by box 122, the error message "improve deployment and continue" will be generated, as discussed above, whereby the amber visual indicator 86 of the distal basket graphic 88 on the user interface 16 will be activated and lighted and a first error tone will be generated by the audible tone generator. In addition, an incomplete treatment cycle will be logged by the digital display 94. Once attempted correction has been made, the footswitch 26 may again be depressed as indicated by user action/input box 124, in which case the treatment cycle is reinitiated.

If on the third or subsequent depression of the footswitch 26 the same error is detected by the system 10, the "check patient circuit" error message will be generated, as discussed above, whereby the amber visual indicator 80 of the return electrode graphic 82 and the amber visual indicator 86 of the electrode basket graphic 88 on the user interface surface 16 will be activated and lighted. Such an error message may also be accompanied by a second audible error tone generated by the audible tone generator. In addition, an incomplete treatment cycle will be logged by the digital display 94. After attempted correction of the error, the footswitch 26 may again be depressed, as indicated by user action/input box 126, in order to initiate another treatment cycle.

Figure 6A:
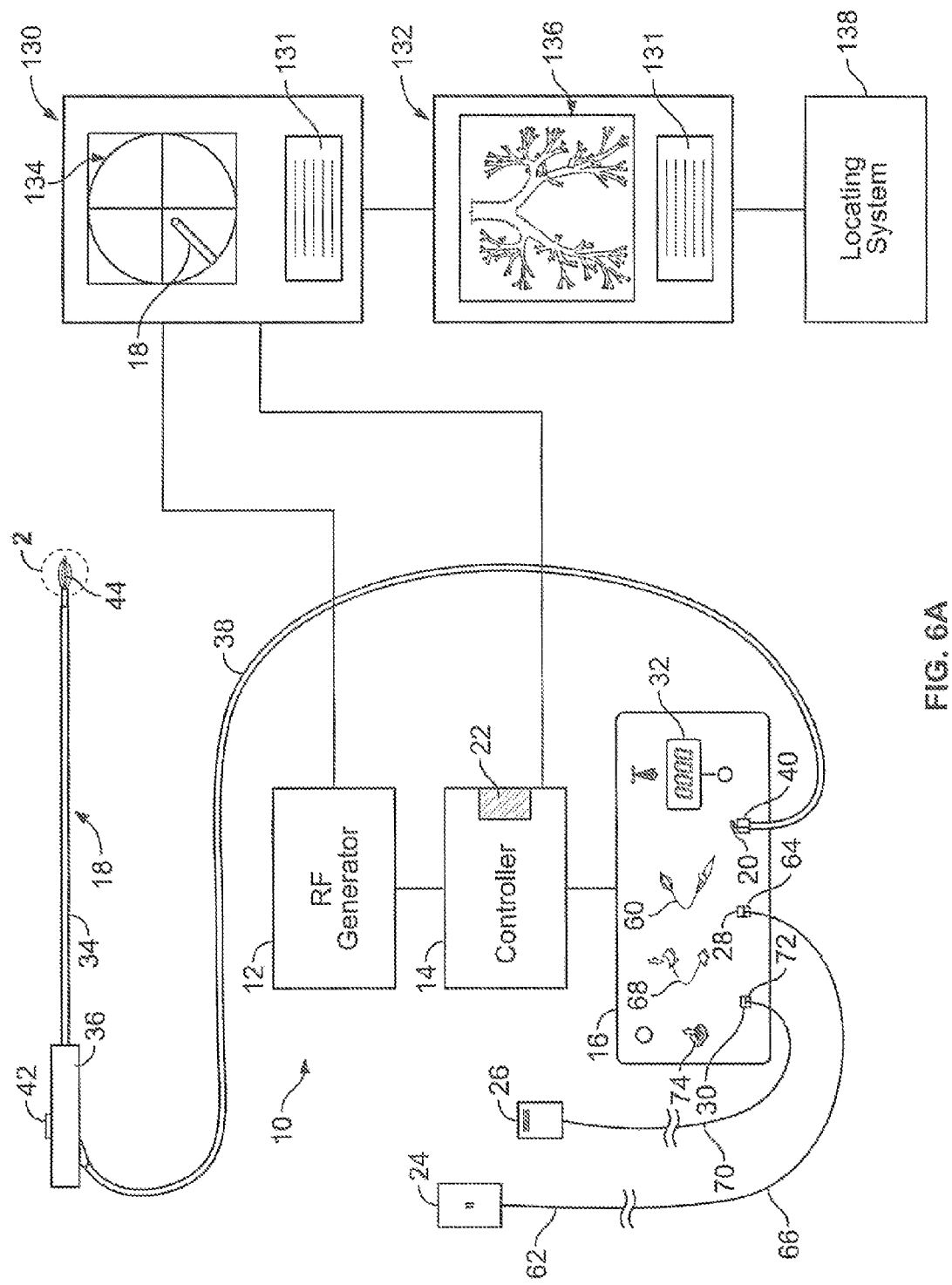
FIG. 6A is a schematic view of a system for delivering energy to the wall tissue of a patient's lung along with the visual and virtual displays.

FIG. 6A shows a system schematic diagram of a system 10 as described herein. The system may have any number of visual displays 130 for displaying treatment information, treatment parameters, virtual maps, positioning, or other data useful to the medical practitioner. For example, many endoscopic procedures include at least one visual display 130 that shows a real-time picture of the target site (and in some cases the tip of the treatment device 18). A map may be projected onto a separate monitor for the virtual display 132 as shown.

The virtual display 132 may comprise an entire virtual map, a virtual treatment location, or a virtual location of the device. Alternatively, the two displays 130 and 132 may be combined so that a virtual display is superimposed onto a visual display or disposed along side of the visual display. However, the map may be also be shown in numerical form (e.g., such as a display of positioning information 131) on either display 130 or 132. It should be noted that the visual display 130 may be any type associated with endoscopic devices (in the case of the lungs—bronchoscopic devices). Furthermore, the visual display may be alternative real-time visual displays (e.g., fluoroscopic or other non-invasive real time imaging means). In another variation of the device, a map may be incorporated into the user interface 16 of the controller 14.

Figure 6B:
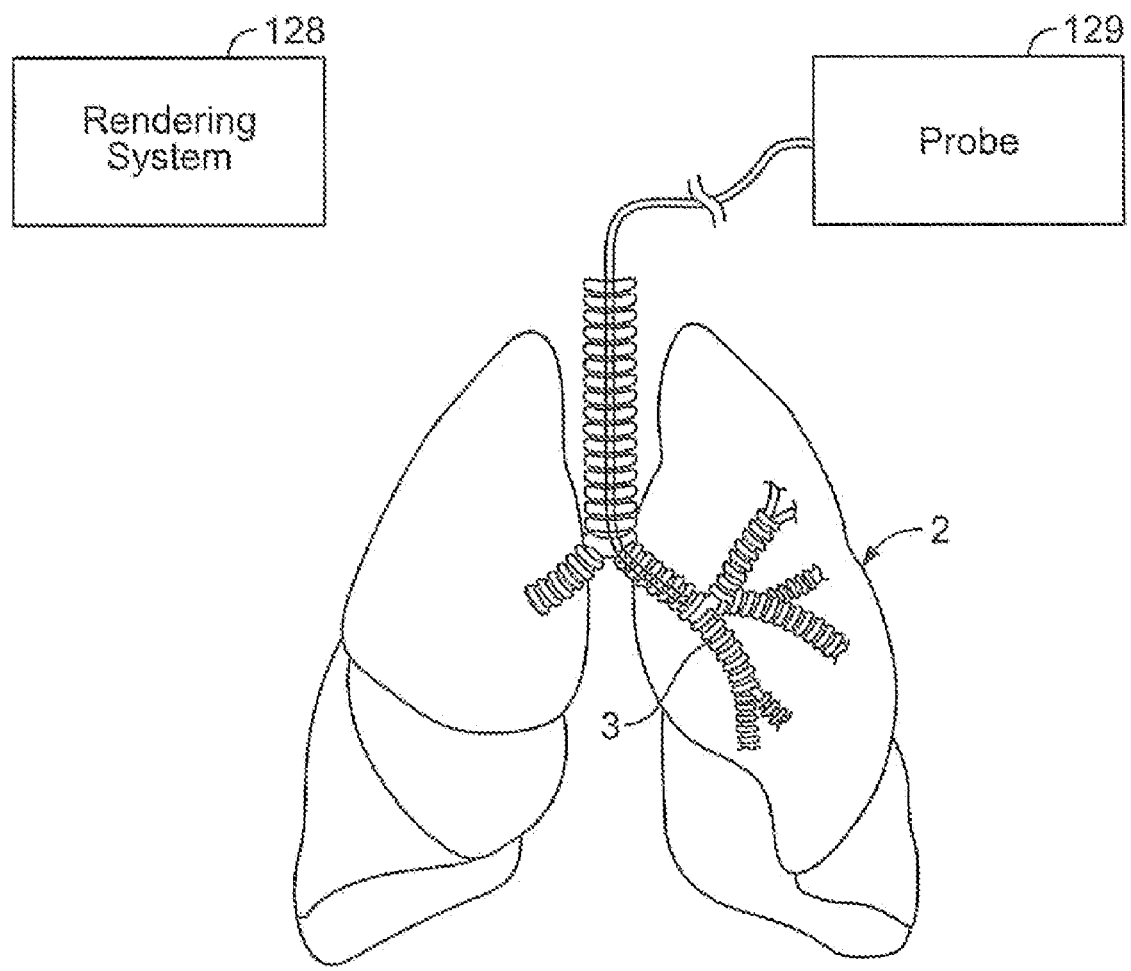
FIG. 6B is a representation of a rendering system for generating a map.

The systems and methods described herein include generating a map of at least a portion of the organ or network of organs (in this case the lungs 2) being mapped using a rendering system as shown in FIG. 6B. Generation of the map may include using a rendering system 128 that includes a computer aided tomography (CT), magnetic resonance imaging (MRI), positron emission tomography (PET), ultrasonic imaging, or other similar rendering system. The rendering system may produce a graphical/virtual map or a map that is purely a series of coordinates relative to a fixed reference point somewhere in the body.

For example, as shown in FIG. 6B, the rendering system 128 may be a system that is external to the body (such as a CT, MRI, PET, etc.). Alternatively, the rendering system may have a probe or other component 129, where the tracking system generates data or coordinates of the probe/device (ultimately the data may be recorded on some storage device) as it travels through the organ. In such a case, until the map data is presented in a virtual map on a display, the map consists of data only. Such a map will be used in systems not having a graphic display such as the one shown in FIG. 1. Instead, these data-only maps may be integrated with the user interface 16, generator 12, or controller 14 to provide a simple signal (audible, visual, or other) during a treatment session to indicate whether the operator has, for example, already treated in the particular area.

The displays 130 and 132 may also be used to provide various information 131 (such as treatment parameters, whether a treatment was previously applied to the location, etc.). Furthermore, the information 131 displayed may also include information from the user interface 16 (as discussed below) thereby eliminating the need for the medical practitioner to constantly shift focus from the user interface 16 to the displays 130 or 132. Although FIG. 6A shows the visual display connected to a generator and controller, any number of configurations is possible. Those shown are for illustrative purposes only.

The map may be rendered/constructed prior to treating the patient or may be rendered as the patient is treated. For example, CT equipment may not be available in the same operating suite as the treatment device. Accordingly, the medical practitioner may use the rendering system to generate the map for use with a later scheduled procedure.

Figure 6C:
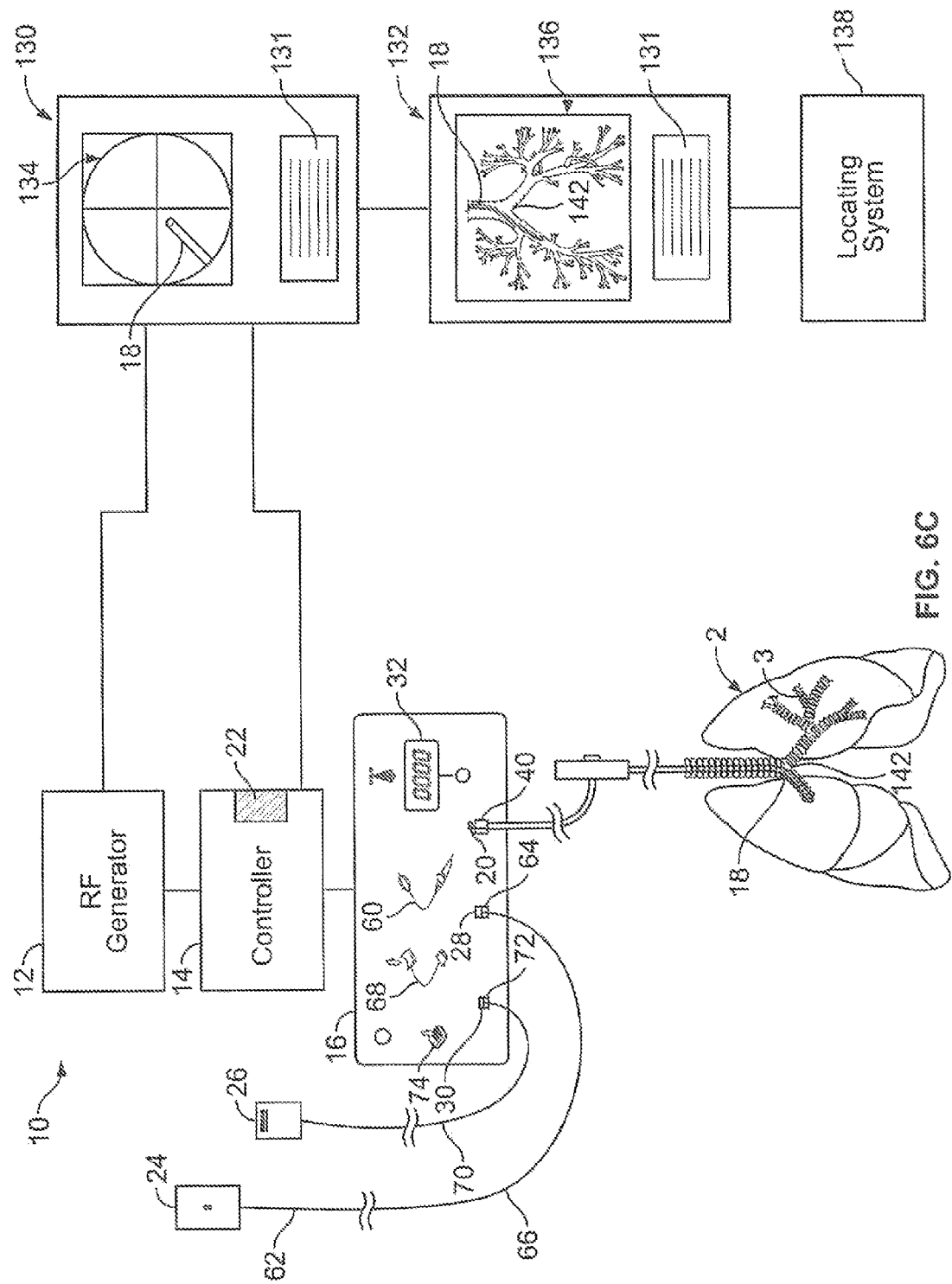
FIG. 6C is a schematic view of a system for delivering energy to the wall tissue of a patient's lung when the device is advanced within the lungs and imaged on the the visual and virtual displays.

In one variation of the invention, as shown in FIG. 6C, once the map is rendered it is correlated and/or oriented with one or more locations in the network of organs. This correlation matches the map data with actual physical sites. One way of orienting the map, is to advance the device 18 into the lung to a known location (e.g., the first bifurcation of the main stem bronchus 142). Once the device 18 is in position, then the user will use the locating system 138 to orient the virtual image of the site (as shown on FIG. 6A) with the actual site. This may be repeated for several sites.

As shown in FIG. 6C, the virtual image 136 shows a virtual map of the airways. As the device 18 advances into the organ, a locating implement (not shown) on the device 18 communicates with a locating system 138 to provide a real position of the device. So long as the virtual map correlates with the actual structure of the organ, an accurate virtual position of the device 18 can be displayed on the virtual map. As discussed herein, as the device 18 applies treatment in the lung 2, the treatment parameters and/or location may be viewed by the medical practitioner no the system 10 or displays 130, 132.

Figure 6D:
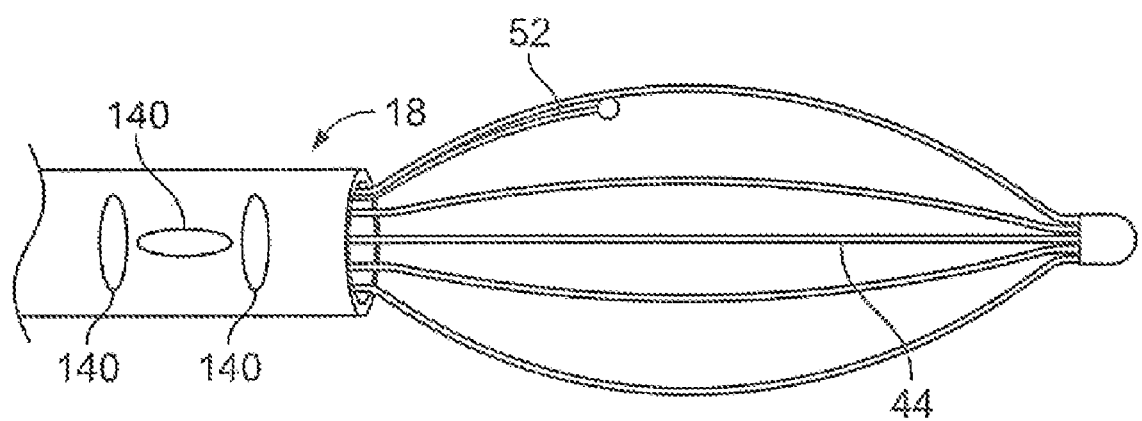
FIG. 6D is an enlarged view of a distal portion of a therapeutic energy delivery device along with elements that enable the mapping of the device within the body.

FIG. 6D illustrates one example of a locating implement 140 coupled to a device 18. The locating implement 140 communicates with the locating system 138 to track the device 18 as it moves within the organ. Examples of such locating implements and systems are found in the references cited and incorporated by reference above.

Furthermore, the treatment system 10, the visual display 130, virtual display 132, and/or locating system 138 may be coupled together such that treatment parameters are associated with their respective treatment sites to generate a treatment history profile for the patient. Naturally, this information may be electronically recorded within the controller 14, locating system 138, or any other component of the system. This previous treatment history profile may be loaded for use during a subsequent treatment session. It may be preferably to store the treatment history profile electronically on a computer system or memory of the controller or even on the rendering system that may be stand alone or integrated in any of the components of the system.

The parameters may include time or duration of treatment, temperature (of the site, the device, or an adjacent site), energy, power, average power, status/incomplete activations, position of treatment, total energy applied, rate of change in temperature, rate of change in applied energy, impedance of the treatment location, or a combination thereof. As noted herein, such parameters may be mapped to treatment locations. It is noted that the parameters and the possible combinations may include those parameters discussed in the patents listed above.

The benefits of the systems and methods described herein allow for improved treatment in an organ that requires treatment at multiple locations or repeat treatments. For instance, generation of the treatment history profile and presenting the parameter data as described herein allows a medical practitioner to potentially avoid overlapping treatment locations or over-treating a particular location. In a variation of the invention, the treatment system may be configured to prevent providing therapy to a particular site if the map and associated parameter(s) indicate that the device is in a location that was previously treated. In such cases, the appropriate audio or visual signals will be shown on either display 130, 132.

Figure 6E:
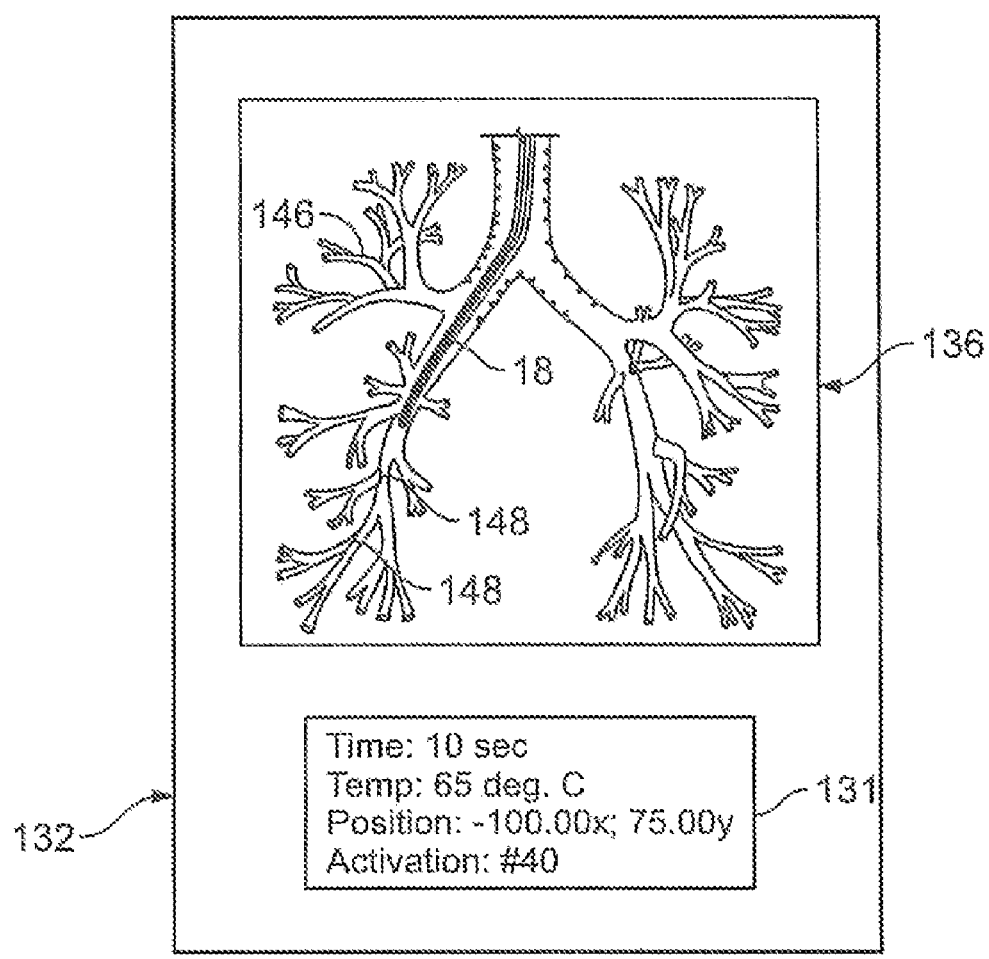
FIG. 6E is a sample view of a virtual map showing the virtual position of the device along with various information to assist the medical practitioner in carrying out the treatment.

Additional benefits include spacing treatment sites at desired intervals and giving a signal to the medical practitioner as to when the device is in the proper location. Moreover, the systems of the present invention may also allow for treatment planning by calculating the shortest distance traveled to give an indication of the next area where the medical practitioner should treat. To accomplish this, the system 10 may provide the appropriate instructions on the displays 130, 132. For example, FIG. 6E illustrates a variation of a virtual display 132. The information displayed 131 is for exemplary purposes only. Variations of the invention include display of any of the parameters discussed herein.

As shown in, FIG. 6E, the virtual map 136 can track the progress of the device 18 as it advances through the organ. The virtual map 136 may also visually differentiate treated areas (for example, the shaded portion 146) from untreated portions. In addition, the virtual map 136 may provide visual information to guide the practitioner to the next site (e.g., via arrow 148). In addition, the virtual map 136 may present information 131 regarding parameters based on the location of the device 18. For example, upon moving to the shaded portion 18 information regarding those treatment parameters would be shown.

The system may allow a user to gain information about where they are, where they've been, and what they've done in different locations. Furthermore, to protect against inadequately treated areas, a second pass of the device, when combined with the map and positioning information, may allow an evaluation of the areas that were not treated, or were inadequately treated. The system may allow for a post treatment analysis where the actual treatment is compared to an "ideal procedure."

In some variations, the controller and/or power supply may be configured such that it will not be able to provide a treatment if the map treatment history profile indicates that the practitioner is about to unintentionally treat a site twice. In some variations, the system may be combined with an auditory signal to indicate some relationship between the current treatment location and the treatment history profile. For example, the auditory signal may give a warning noise if the treatment was incomplete/already performed and every time the locating implement passes over that particular site, the same signal would be triggered.

The treatments may also be titrated based on analysis of the map or on the analysis of other anatomical data. For example, if the map yields an organ having varying wall thicknesses, algorithms may be used to tailor the parameters of the treatment (e.g., thicker walled sections receiving higher energy treatment and thinner sections receiving lower energy.) The titration may be based on the depth at which the intended target resides. For example, if smooth muscle tissue is located deep within the organ walls, the titration may adjust energy parameters for optimal treatment. In another example, the energy parameters may be reduced if the mapping or other analysis indicates that the target area is proximate to another vital organ.

The system of the present invention may also provide a visual identification of the organ or area to be treated. For example, if a site has already been treated, the organ may be shown in a particular color and to signal an area that has not been treated, the target organ may be shown in another color. If the system determines that a particular site should be treated next, this suggested treatment location may also be visually distinguished on the visual displays 130, 132.

The system may also allow for the generation of an ideal procedure or procedure profile based on the map. For example, use of the map may allow various characteristics to be determined about the target area or organ (e.g., diameter of the passage, amount of smooth muscle tissue, bifurcations, etc.). Based on these characteristics, the energy treatment may be tailored for a set of ideal parameters. Therefore, a medical practitioner may compare the parameters of the actual treatment (using the treatment history profile) to the ideal parameters based on the ideal procedure. In the case of discrepancies, the medical practitioner has the option to retreat areas or simply observe areas where actual treatment differs from an ideal treatment. The ideal parameters may be the same type of parameters as those described above. For example, they may include an ideal treatment time, ideal temperature, ideal energy, ideal rate of change in temperature, ideal rate of change in energy, ideal impedance of the treatment location, and a combination thereof. The system may allow for comparison of an ideal procedure to the actual procedure may occur during the procedure or after the procedure.

As noted above, the map may permit analysis of the body and structures surrounding the target area for improved treatments. In one example, the system may use algorithms for analyzing the body to determine an anatomical characteristic of the area being treated such that a therapy may be delivered that is tailored for the anatomical characteristic. For example, the anatomical characteristic may include the luminal passageway diameter, branching points of the organs, depth of smooth muscle tissue, amount of smooth muscle tissue, wall thickness of the organ, proximity of the organ relative to a separate organ, periphery of the organs, degree of fluids in the organ, number of folds in the organ, condition of an epithelial or endothelial layer in the organ, fluid flow in the organ, presence of additional tissue in the organ, presence of vessels, presence of cartilage, and degree of contraction when the smooth muscle is stimulated. Such anatomic characteristics may be identified during the rendering of the map as shown in FIG. 6C.

Apart from creating an ideal procedure, the procedure may be adjusted in a real time basis in response to the particular anatomical feature that is identified on the map. When the treatment device is placed on an actual treatment site, this system may trigger the control system to alter one or more of the energy or other parameters.

It should be noted that the map may be constructed to be a three-dimensional map (for example, the bronchial passages branch in many directions requiring a three dimensional map for proper imaging.) Alternatively, it may be desired to only generate a map of a single plane.

In another variation of the invention, the aspects of the above systems described herein may be combined with a device having an energy delivery portion that is used to apply energy therapy to the treatment location, and where the treatment device transmits information to the rendering system to generate at least a portion of the map as it advances through the network of organs. In such a case, the rendering system may simply track the movements of the device in the body. For example, the device may comprise a sensor assembly similar to that used in optical tracking devices (such as an optical computer mouse.) In this manner, the map is rendered as the treatment progresses.

For example, a sensor assembly on or connected to the treatment device may be in communication with the rendering system and allow for detection of movement of the device within the organs to generate the portion of the map. In one variation, the sensor assembly as shown by 140 in FIG. 6D, may comprise a light emitting source, a sensor, and a digital signal processor where the light emitting source reflects light off of a wall of the organ to the sensor and the sensor transmits a plurality of images to the digital signal processor which determines movement of the device by comparing images, intensities, and/or wavelengths of the reflected light. As an example, the light emitting source may comprise a light emitting diode and the sensor may comprise a complimentary metal-oxide semiconductor (CMOS). However, any known configuration may be used. In some variations, the configurations may permit tracking as the device advances through the network of organs. An example of the placement of the sensor assembly may be found on FIG. 6C. In most cases, the sensor assembly and locating implements will be found on the distal ends of the devices.

In those cases where it is difficult to generate a 3 dimensional map, the treatment device further includes at least one locating implement that communicates with an external locating system to generate the portion of the map allowing for a 3 dimensional construction.

In yet another variation of the invention, the invention includes a method of creating a map in a network of connected organs, each having a luminal passageway, the method comprising advancing a device into the network of organs, where the device comprises a light emitting source, a sensor, and a digital signal processor; generating data to characterize movement of the device in the network of organs where the light emitting source reflects light off of a wall of the organ to the sensor and the sensor transmits a plurality of images to the digital signal processor which determines movement of the device by comparing images; and transmitting the data to an electronic storage means.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method for treating smooth muscle tissue surrounding a luminal passageway in an asthmatic lung of a patient, the method comprising:
generating a map representing at least a portion of luminal passageways in the lung using a rendering system;
selecting at least one treatment location within the luminal passageway of the lung, wherein a substantial portion of the map is generated before selecting at least one treatment location;
providing a separate real-time visual display module displaying the treatment location from within the luminal passageway of the lung via a bronchoscope, wherein an actual position of the treatment location on the map and the separate real-time visual display module displaying the luminal passageways are displayed concurrently;
applying an energy therapy to the treatment location to treat the smooth muscle tissue, where the energy therapy applied to the respective treatment location is defined by a plurality of parameters; and
generating a treatment history profile where the treatment history profile includes a virtual position of the device at each treatment location when applying the energy therapy.

2. The method of claim 1, further comprising correlating the map with a plurality of locations in the lung.

3. The method of claim 1, further comprising using the actual position of the treatment location on the map to select the treatment location.

4. The method of claim 1, further comprising imposing at least a portion of the map on the real-time visual display from within the luminal passageway.

5. The method of claim 1, further comprising advancing a device into the lung, where the device comprises at least one locating implement that communicates with a locating system to establish the virtual position of the device on the map.

6. The method of claim 5, where displaying the real time image of the luminal passageways on the visual display includes imposing the virtual position of the device on the visual display.

7. The method of claim 5, further comprising displaying the map and the virtual position of the device on a monitor.

8. The method of claim 5, where applying the energy therapy comprises inserting an energy delivery element into the lung where the energy delivery element is coupled to a control system configured to provide energy for the energy therapy.

9. The method of claim 8, where the energy delivery element is affixed to a treatment device.

10. The method of claim 8, where the energy delivery element is affixed to the device.

11. The method of claim 10, further comprising applying the energy therapy with the device at a plurality of treatment locations.

12. The method of claim 1, where the treatment history profile is electronically recorded.

13. The method of claim 1, where the treatment history profile further includes at least one of the plurality of parameters of the respective energy therapy associated with the virtual position of the device at each treatment location.

14. The method of claim 1, where displaying at least a portion of the treatment history profile allows a medical caregiver to avoid overlapping treatment locations when applying one or more energy therapies.

15. The method of claim 14, where the control system is prevented from providing the energy therapy if the medical caregiver overlaps treatment locations.

16. The method of claim 1, further comprising providing an auditory output to signal a relationship between a current treatment location and the treatment history profile.

17. The method of claim 1, further comprising displaying at least a portion of the treatment history profile on either the monitor or the visual display.

18. The method of claim 17, where displaying the treatment history profile comprises visually marking a portion of the luminal passageway on the visual display to identify a previous treatment site.

19. The method of claim 18, where visually marking the portion of the luminal passageway comprises coloring the portion of the luminal passageway on the visual display.

20. The method of claim 17, further comprising providing a suggested treatment location on either the visual display or the monitor.

21. The method of claim 20 where the control system is prevented from providing the energy therapy if a medical caregiver fails to apply the energy therapy to the suggested treatment location.

22. The method of claim 20, where providing the suggested treatment location comprises visually distinguishing a location of the luminal passageway from portions of the luminal passageway that correspond to the treatment history profile.

23. The method of claim 22, where the suggested treatment location does not overlap with portions of the luminal passageway that correspond to the treatment history profile.

24. The method of claim 23, where the suggested treatment location is spaced from portions of the luminal passageway that correspond to the treatment history profile.

25. The method of claim 20, where providing the suggested treatment location comprises using the map to calculate a minimum distance to a neighboring organ or anatomical marker.

26. The method of claim 25, where providing the suggested treatment location further comprises displaying a suggested path on either the visual display or monitor, where the suggested path comprises directions through the lung to reach the suggested treatment location.

27. The method of claim 25, further comprising calculating a minimum time based on an algorithm that minimizes a factor of time, difficulty of navigation, or size difference between organs.

28. The method of claim 1, further comprising generating an ideal procedure profile based on the map, where the ideal procedure profile comprises a plurality of ideal parameters.

29. The method of claim 28, where the plurality of ideal parameters includes at least one ideal virtual treatment location.

30. The method of claim 29, where the plurality of ideal parameters further includes at least one ideal energy therapy parameter associated with the respective ideal virtual treatment location.

31. The method of claim 30, where the ideal energy therapy parameters comprise parameters selected from the group consisting of ideal time, ideal temperature, ideal energy, ideal rate of change in temperature, ideal rate of change in energy, ideal impedance of the treatment location, and a combination thereof.

32. The method of claim 28, further comprising comparing the ideal procedure profile to the treatment history profile.

33. The method of claim 32, where comparing the ideal procedure profile to the treatment history profile occurs during applying the energy therapy to the treatment location.

34. The method of claim 1, further comprising analyzing the map to determine an anatomical characteristic of the lung.

35. The method of claim 34, where the anatomical characteristic comprise features selected from the group consisting of luminal passageway diameter, branching points of the organs, depth of smooth muscle tissue, amount of smooth muscle tissue, wall thickness of the organ, proximity of the organ relative to a separate organ, periphery of the organs, degree of fluids in the organ, number of folds in the organ, condition of an epithelial or endothelial layer in the organ, fluid flow in the organ, presence of additional tissue in the organ, presence of vessels, presence of cartilage, and degree of contraction when the smooth muscle is stimulated.

36. The method of claim 35, where the energy therapy is generated by a control system and where the control system adjusts at least one of the plurality of parameters in response to the anatomical features.

37. The method of claim 1, where the map is a three dimensional map.

38. The method of claim 1, where the plurality of parameters comprises at least one of time, temperature, energy, rate of change in temperature, rate of change in energy, and impedance of the treatment location.

39. The method of claim 38, further comprising displaying at least one parameter of the energy therapy on the visual display.

40. The method of claim 39, where displaying at least one parameter of the energy treatment occurs in real time during the application of energy.

41. The method of claim 1, where the lung comprises airways within a lobe of the lung, and the method further comprises applying the energy therapy to a plurality of airways.

42. The method of claim 1, where a treatment device having an energy delivery portion is used to apply energy therapy to the treatment location, and where the treatment device transmits information to the rendering system to generate at least a portion of the map as it advances through the lung.

43. The method of claim 42, further comprising correlating the portion of the map with a plurality of locations in the lung.

44. The method of claim 42, where the treatment device further includes a sensor assembly in communication with the rendering system and that detects movement of the device within the organs to generate the portion of the map.

45. The method of claim 44, where the sensor assembly comprises a light emitting source, a sensor, and a digital signal processor where the light emitting source reflects light off of a wall of the organ to the sensor and the sensor transmits a plurality of images to the digital signal processor which determines movement of the device by comparing images.

46. The method of claim 45, where the light emitting source comprises a light emitting diode and the sensor comprise a complimentary metal-oxide semiconductor.

47. The method of claim 42, where the treatment device further includes at least one locating implement that communicates with an external locating system to generate the portion of the map.

* * * * *

UNITED STATES PATENT AND TRADEMARK OFFICE
CERTIFICATE OF CORRECTION

PATENT NO. : 7,594,925 B2 Page 1 of 1
APPLICATION NO. : 11/408668
DATED : September 29, 2009
INVENTOR(S) : Christopher J. Danek et al.

It is certified that error appears in the above-identified patent and that said Letters Patent is hereby corrected as shown below:

In column 1, line 39-40, after "entirety." delete "each of which is incorporated by reference in their entirety.".

In column 2, line 26, delete "bronchiodilators." and insert -- bronchodilators. --, therefor.

In column 2, line 28, delete "bronchiodilators." and insert -- bronchodilators. --, therefor.

In column 6, line 27, after "the" delete "the".

In column 9, line 52, delete "mode" and insert -- mode. --, therefor.

In column 21, line 19, claim 24, delete "lurninal" and insert -- luminal --, therefor.

Signed and Sealed this

Sixteenth Day of February, 2010

David J. Kappos
*Director of the United States Patent and Trademark Office*